United States Patent [19]

Pierce et al.

[11] Patent Number: 5,032,505
[45] Date of Patent: Jul. 16, 1991

[54] INHIBITORS FOR GLYCOSAMINOSYL TRANSFERASE V

[75] Inventors: James M. Pierce, Miami, Fla.; Ole Hindsgaul, Edmonton, Canada

[73] Assignee: Chembiomed, Ltd., Edmonton, Canada

[21] Appl. No.: 274,069

[22] Filed: Nov. 21, 1988

[51] Int. Cl.$^5$ .................. C12Q 1/48; C12N 9/10; C07H 15/02; A61K 31/70
[52] U.S. Cl. ...................................... 435/15; 536/4.1; 536/53; 435/193; 436/64; 436/501; 436/578; 436/813; 514/25
[58] Field of Search ............... 536/4.1, 53; 435/15, 435/193; 436/64, 501, 518, 813; 514/25

[56] References Cited

U.S. PATENT DOCUMENTS 4,770,994 9/1988 Rittenhouse .................. 435/15

FOREIGN PATENT DOCUMENTS 0134292 3/1985 European Pat. Off. .
0272603 6/1988 European Pat. Off. .
64-42496 2/1989 Japan .
8902474 3/1989 World Int. Prop. O. .

OTHER PUBLICATIONS

Ahrens et al., *J. Biol. Chem.* (1987), 262:7575.
Camarasa et al., *J. Med. Chem.* (1985) 28:40.
Cummings et al., *J. Biol. Chem.* (1982), 257:11230.
Dennis, *Cancer Res.* (1986) 46:5131.
Dennis, *Cancer Surveys* (1988).
Dennis et al., *Science* (1987) 236:582.
Humphries et al., *Science (1986) 233:467.*
Irimura et al., *Cancer Res.* (1981) 41:3411.
Kijima-Suda et al., *Cancer Res.* (1986) 46:858.
Pierce et al., *J. Bio. Chem.* (1986) 261:10772.
Schacter, *Biochem. Cell. Bio.* (1986) 64:163.
Vaghefi et al., *J. Med. Chem.* (1987) 30:1391.
Yamashida et al., *J. Bio. Chem.* (1984) 259:10834.
Yamashida et al., *J. Bio. Chem.* (1985) 260:3963.
Srivastava et al., *Carbohydrate Res.* (1988) 179:137–161.
Palcic et al.; Glycoconjugate Journal 5:49–63 (1988).
Khare et al.; Carbohydrate Research 136:285–308 (1985).
Shah et al.; Carbohydrate Research 153: 155–161 (1986).
Tahir et al.; Canadian Journal of Chemistry 64:1771–1780 (1986).
Pierce et al.; Biochemical and Biophysical Research Communications 146(2): 679–684 (7/31/87).
Hindsgaul et al.; Carbohydrate Research 173: 263–272 (3/1/88).

*Primary Examiner*—Ronald W. Griffin
*Assistant Examiner*—Nancy S. Carson
*Attorney, Agent, or Firm*—Irell & Manella

[57] ABSTRACT

Synthetic glycosaminosyl transferase-V acceptors and inhibitors are disclosed. Minimal trisaccharide inhibitors and acceptors specific for GnT-V, which is associated with the ability of cells to metastasize are useful, in diagnosis and treatment of conditions characterized by metastatic cells.

18 Claims, 7 Drawing Sheets

1: $R_1$=H, $R_2$=H

2: $R_1$=Bn, $R_2$=H

3: $R_1$=OMe, $R_2$=H, $R_3$=H, $R_4$=OH

4: $R_1$=OMe, $R_2$=H, $R_3$=Ac, $R_4$=I

5: $R_1$=OMe, $R_2$=H, $R_3$=Ac, $R_4$=H

6: $R_1$,$R_2$=Ac, $R_3$=Ac, $R_4$=H

7: $R_1$=Br, $R_2$=H, $R_3$=Ac, $R_4$=H

8: R=Ac

9: R=H

10: R=Bn

11

12: R=Ac

13: R=H

14

15: $R_1$=Bn, $R_2$=Phth, $R_3$=Ac

16: $R_1$=Bn, $R_2$=H,Ac, $R_3$=Ac

17: $R_1$=Bn, $R_2$=H,Ac, $R_3$=H

H : $R_1$=H, $R_2$=H,Ac, $R_3$=H

INHIBITORS FOR GLYCOSAMINOSYL TRANSFERASE V

TECHNICAL FIELD

The invention relates to therapy and diagnosis of metastatic metabolic states using inhibitors of a glycosaminosyl transferase (GnT) which has elevated levels associated with metastasis. In particular, the invention relates to methods to treat and diagnose a cellular metastatic state employing inhibitors of the specific glycosyl transferase GnT-V.

BACKGROUND ART

Cell surfaces of both normal and tumor cells are characterized by a plethora of carbohydrate structures resulting from the glycosylation of lipids and proteins. In general, it is recognized that the glycosylation patterns exhibited by tumor cells and by normal cells are markedly different. More than a dozen tumor-associated glycosydic structures, including Le$^a$, sialyl-Le$^a$, Le$^x$, and sialyl-Le$^x$ have been described. It is also characteristic of the transition from normal to transformed (tumor) cell that the size of asparagine linked (N-linked) oligosaccharides is markedly increased, and occurrence of high molecular weight fucosylated N-linked oligosaccharides is a reproducible correlate with malignant transformation.

In particular, it has been shown that there is a correlation between the degree of increase in beta(1-6) branching of N-linked oligosaccharides and the metastatic potential of murine and human tumor cells (Dennis, J. W., *Cancer Surveys* (1988) in press; Dennis, J. W., et al, *Science* (1987) 236:582).

It has also been shown that tumor cell mutants deficient in GnT-V, and therefore in the large, highly branched cell surface carbohydrates are dramatically decreased in their metastatic potential (Dennis, J. W., et al, *Science* (1987) 236:582 (supra)). Studies on BHK cells transformed with the polyoma DNA papovavirus, or with the RNA retrovirus Rous sarcoma virus, showed that transformation resulted in an increase in branching at the glycosylation acceptor trisaccharide portion of the glycoside, beta-GlcNAc(1-2)alpha-Man(1-6)beta-Man→(Yamashida, K., et al, *J Biol Chem* (1984) 259:10834; Yamashida, K., et al, *J Biol Chem* (1985) 260:3963; Pierce, M., et al, *J Biol Chem* (1986) 261:10772).

The increase in branching at this trisaccharide portion was correlated with an increase in the activity of N-acetyl glucosaminyl transferase-V (GnT-V, EC 2.4.1.155), which catalyzes the branching of the foregoing trisaccharide portion contained in N-linked carbohydrates by transfer of an acetyl glucosamine residue from UDP-GlcNAc into a 1-6 linked branch with the alpha-mannosyl residue of this trisaccharide portion in the context of Reaction Scheme I (Cumming, R. D., et al, *J Biol Chem* (1982) 257:11230).

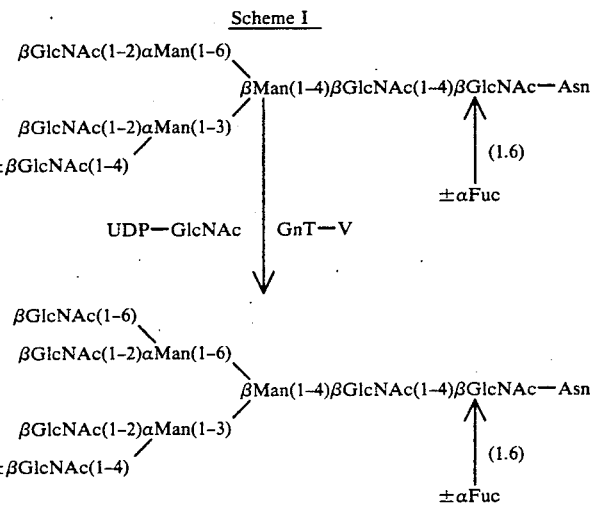

REACTION SCHEME 1

While not intending to be bound by any theory, applicants believe it is possible that the branching catalyzed by GnT-V is a prerequisite for the formation of large tumor-associated N-linked glycosylation chains by subsequent glycosyl transfers catalyzed by a number of other enzymes, as summarized in Reaction Scheme 2.

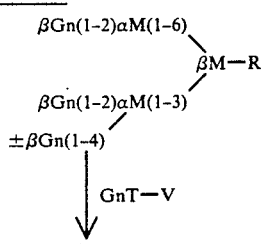

-continued

Scheme II

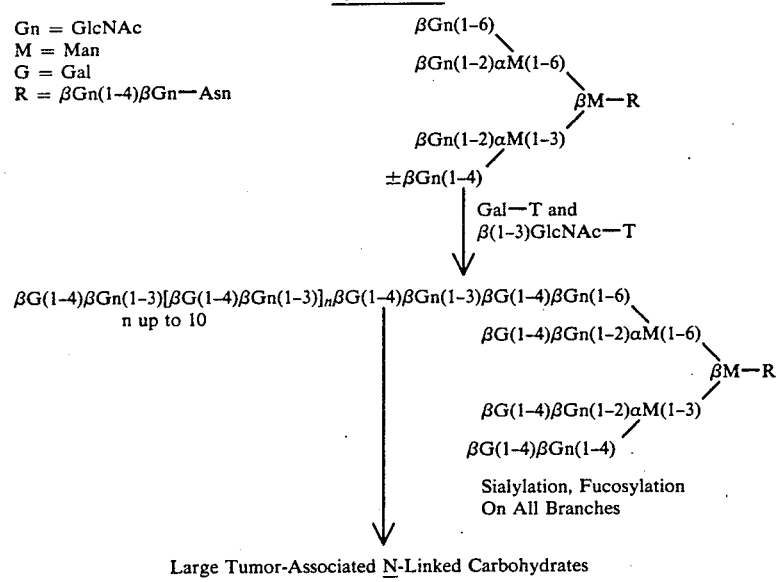

Gn = GlcNAc
M = Man
G = Gal
R = βGn(1-4)βGn—Asn

REACTION SCHEME 2

It further may be the case that the presence of the large and complex glycosylation residues on tumor cells interferes with the interaction of the normal cell surface tripeptide (RGD) receptors with binding to extracellular matrix glycoproteins.

Consistent with this theory, drugs which interfere with glycosylation have been shown to affect the growth of tumor cells. For example, tunicamycin, which inhibits all N-linked glycosylation, and the alkaloids castanospermine and swainsonine, which distort glycosylation pattern by resulting in production of only high mannose oligosaccharides with incomplete N-acetyl glucosamine branching, have been shown to inhibit organ colonization by B16 melanoma (Irimura, T., et al, *Cancer Res* (1981) 41:3411; Humphries, M. J., et al, *Science* (1986) 233:467; Dennis, J. W., *Cancer Res* (1986) 46:5131). Swainsonine has also been shown to inhibit colonization by metastatic MDAY-D2 lymphoma cells (Dennis, J. W., *Cancer Surveys* (1988), in press), to reduce tumor cell growth rate in soft agar, and to enhance susceptibility of tumor cells to natural killer cells (Ahrens, P. B., et al, *J Biol Chem* (1987) 262:7575).

To applicants knowledge, known inhibitors of the active sites for the GnT family are restricted to sugar nucleotide analogs to the glycosyl donor moieties (Camarasa, M., et al, *J Med Chem* (1985) 28:40; Vaghefi, M. Y., et al, *J Med Chem* (1987) 30:1391; Kijima-Suda, I., et al, *Cancer Res* (1986) 46:858), and one of these, a CMP-sialic acid analog has anti-tumor activity (Kijima-Suda et al, supra). This approach to inhibition of GnT-V, i.e., use of analogs of the UDP-GlcNAc donor as inhibitors would be expected to be relatively nonspecific and to inhibit all of the 9 known GlcNAc transferases involved in the synthesis of N-linked oligosaccharides (Schacter, H., *Biochem Cell Biol* (1986) 64:163), as well as those GnTs involved in glycolipid biosynthesis.

Thus, the invention approach, which focuses on the acceptor moiety for the GnT-V catalyzed reaction, offers inhibition of an enzyme specifically correlated with metastatic capability of tumor cells.

DISCLOSURE OF THE INVENTION

The invention provides synthetic acceptors and inhibitors for the enzyme N-acetyl glucosaminyl transferase-V (GnT-V) which is found at elevated levels in tumor cells, especially in metastatically active tumor cells. These synthetic acceptors and inhibitors provide materials for convenient methods to assay the levels of GnT-V in sample cells suspected of being metastatic. In addition, the inhibitors are useful therapeutically to reduce the effect of GnT-V in cells which have elevated levels of this enzyme and/or which show metastatic characteristics.

Thus, in one aspect, the invention is directed to compounds which are synthetic acceptors for GnT-V, said compounds having the formula beta-GlcNAc(1-2)alpha-Man(1-6)X   (1)

wherein X is a beta-glycopyranose or a derivative thereof, said glycopyranose or derivative represented by X being of such structure as not to cause an essential change in the character of the compound of Formula 1 as an effective acceptor.

(Although not necessarily specifically denoted in the formula designations and nomenclature herein, all of the sugar residues are in the D-configuration unless specifically noted otherwise.)

In other aspects, the invention is directed to methods to assess the level of GnT-V in a sample, especially a sample of cells, which method comprises measuring the transfer of beta-GlcNAc from UDP-GlcNAc to the acceptor of Formula 1.

In another aspect, the invention is directed to inhibitors of GnT-V of the formula beta-GlcNAc(1-2)alpha-6-deoxy-Man(1-6)X   (2A)

4-Fl-beta-GlcNAc(1-2)alpha-6-deoxy-Man(1-6)X   (2B), or 4-deoxy-beta-GlcNAc(1-2)alpha-6-deoxy-Man(-1-6)X   (2C)

wherein X is a beta-glycopyranose or derivative thereof, wherein said glycopyranose or derivative does not materially affect the ability of the compounds of Formulas 2A-2C to behave as inhibitors for GnT-V.

In other aspects, the invention is directed to methods to measure the level of GnT-V in a sample, especially in a sample of cells, which method comprises measuring the effect of any of the compounds of Formulas 2A-2C on transfer of beta-GlcNAc from UDP-GlcNAc to the mixtures of acceptors which occur in cellular extracts. As these inhibitors are specific for GnT-V, inhibition will occur only if that enzyme is present.

Still another aspect of the invention is a method to inhibit the metastatic activity of tumor cells in a subject which method comprises administering to a subject in need of such treatment an amount of one or more of the inhibitors of Formulas 2A-2C, or pharmaceutical compositions thereof, effective to result in such inhibition. The invention is also directed to pharmaceutical compositions for this purpose in which the active ingredient is one or more of these compounds.

In another aspect, the invention is directed to compounds of the formula:

2-deoxy-beta-Gal(1–4)beta-GlcNAc-OY       (3)

wherein Y is a hydrophobic substituent as further described herein below, which compounds are inhibitors of a fucosyl transferase which transfers alpha-L-fucose from GDP-fucose to portions of glycosides which contain the nondeoxy analog of the compounds of Formula 3. Thus, the normal acceptor for the alpha-L-fucose is of the formula beta-Gal(1–4)beta-GlcNAc, as contained in a glycoside chain. The product of the fucosyl transfer is associated with the human blood group antigen H Type II.

MODES OF CARRYING OUT THE INVENTION

Acceptors, Inhibitors and Preferred Embodiments

Figure 1A:
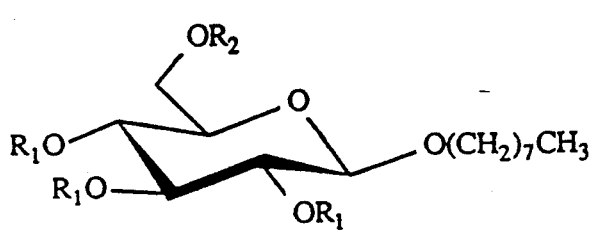
FIG. 1 shows the structures of various intermediates in the synthesis of an illustrative compound of Formula 2.
Figure 1A:
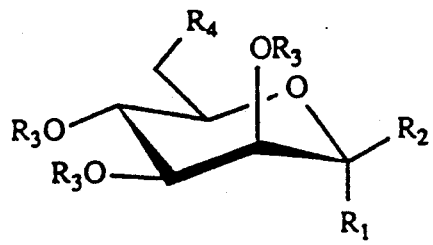
Figure 1A:
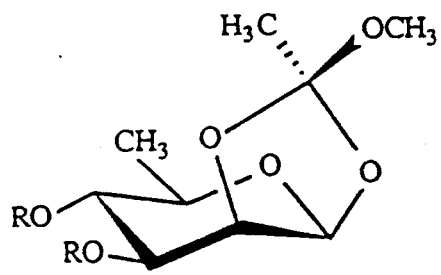
Figure 1A:
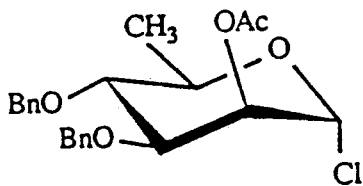
Figure 1B:
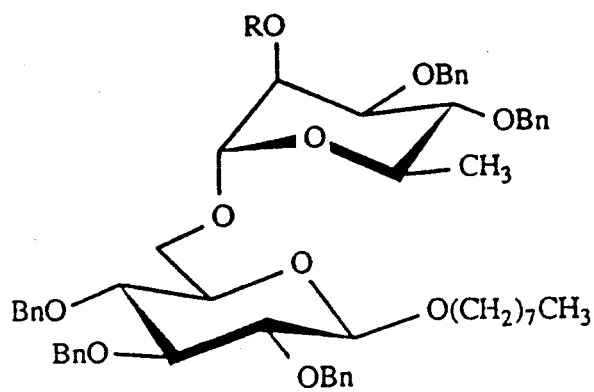
Figure 1B:
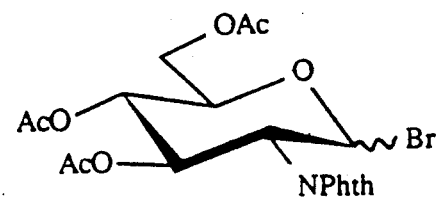
Figure 1B:
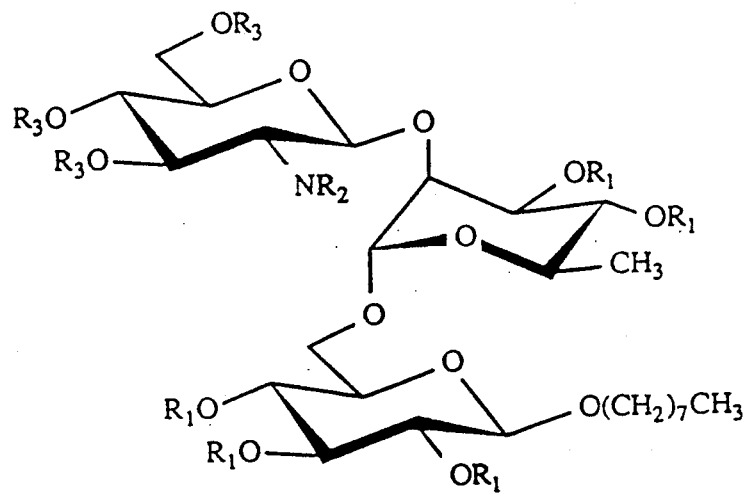
Figure 2A:
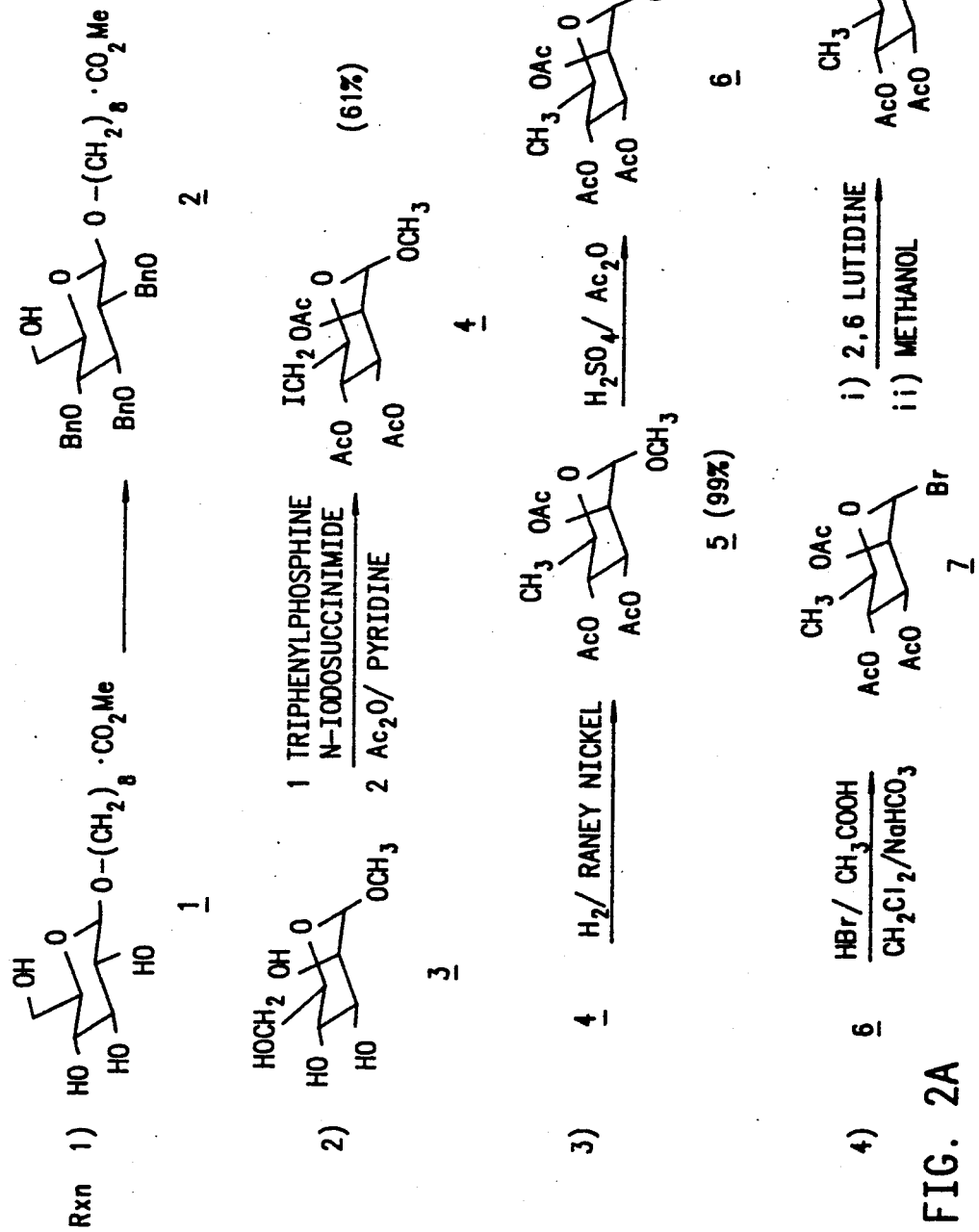
FIG. 2 shows the steps in the synthesis of the illustrative compound for which intermediates are shown in FIG. 1.
Figure 2B:
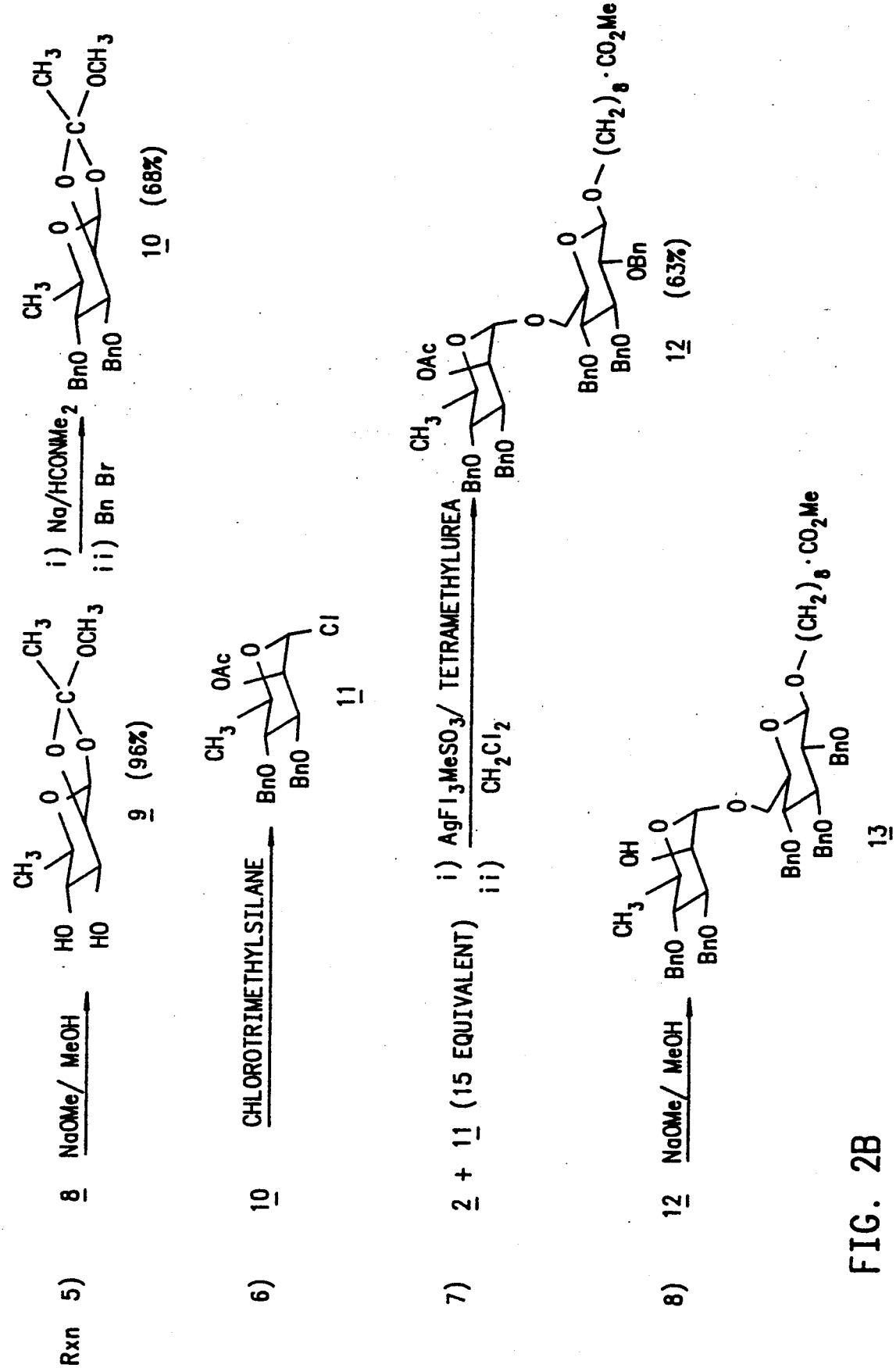
Figure 2C:
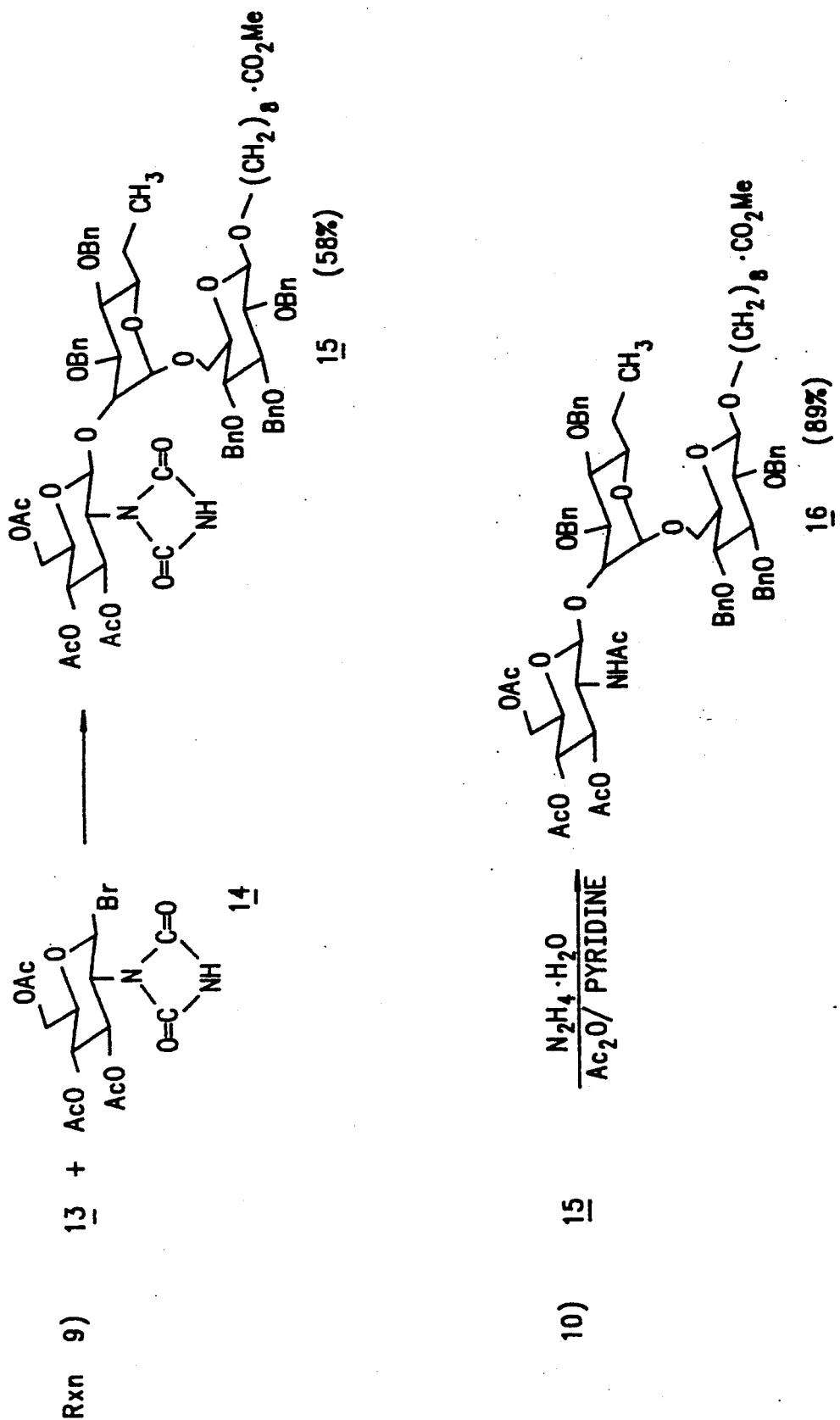
Figure 2D:
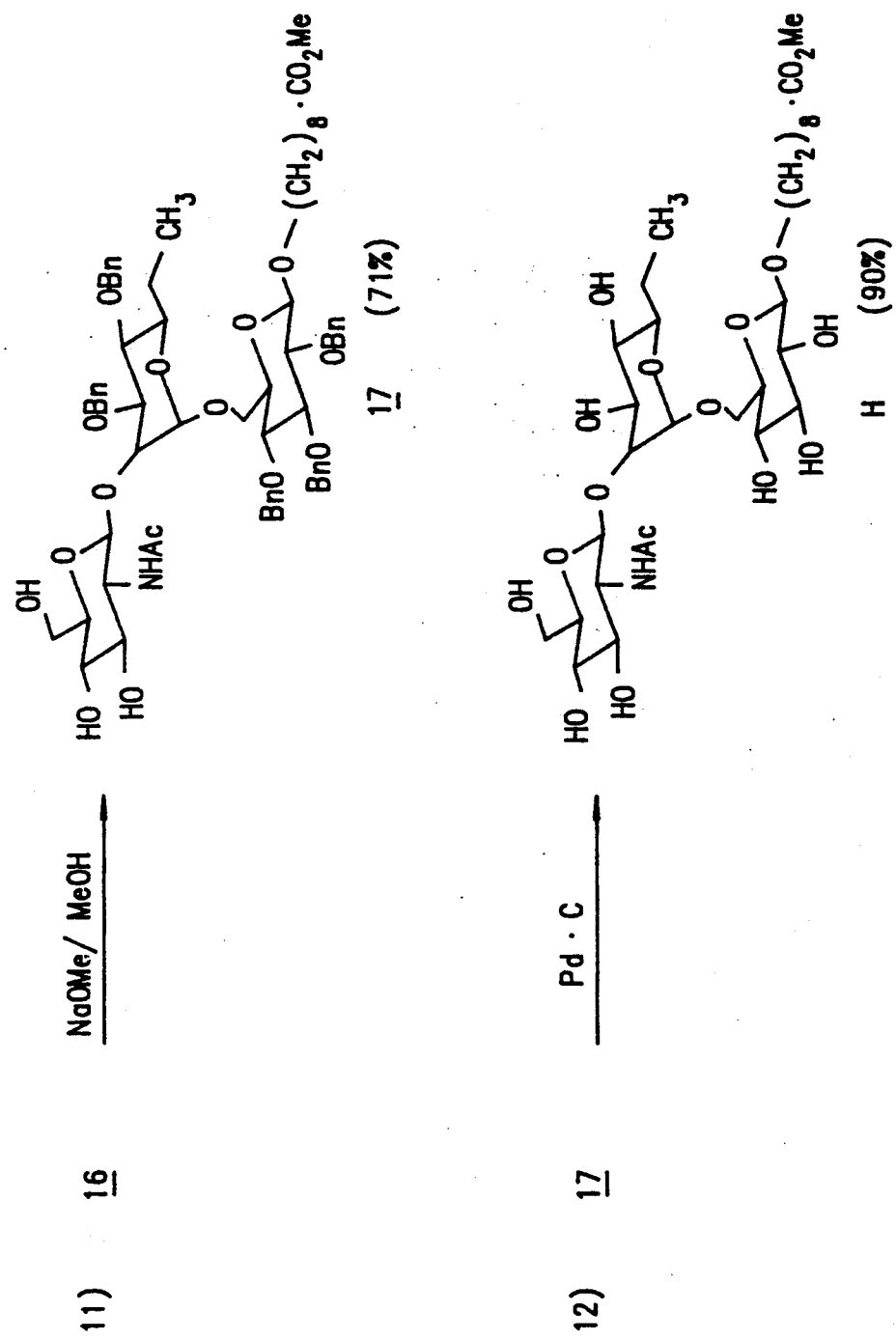

The acceptors and inhibitors for GnT-V of the invention are beta (1-6) glycosides of beta-GlcNAc(1-2)alpha-Man (for acceptors) or of beta-GlcNAc(1-2)alpha-6-deoxy-Man, or 4-Fl-beta-GlcNAc(1-2)alpha-6-deoxy-Man, or 4-deoxy-beta-GlcNAc(1-2)alpha-6-deoxy-Man (for inhibitors). The acceptors and inhibitors of the invention differ only in that the alpha-mannoside residue is in the deoxy form in the inhibitor, thus rendering the compounds of Formulas 2A-2C incapable of behaving as an acceptor for an additional beta-GlcNAc residue transferred in a reaction catalyzed by GnT-V.

In addition, in the inhibitors, the beta-GlcNAc residue may be present as the 4-fluoro or 4-deoxy derivatives, formulas 2B and 2C respectively, as these modifications prevent transfer to the inhibitor of a galactosyl residue at the 4 position, which is a succeeding step in the normal course of glycoside chain building as indi- cated in Scheme II above. Transfer of a galactosyl residue to position 4 of the inhibitor results in destruction of the inhibition activity. Accordingly, the inhibitors of Formulas 2B and 2C are protected from this deactivation by substitution of the 4-fluoro or 4-deoxy derivatives for the GlcNAc residue of the compound of Formula 2A.

Both acceptors and inhibitors require 1-6 glycosylation by the moiety represented as "X" herein, wherein X is a beta-glycopyranose or derivative thereof. Preferably, X is a glucopyranose or mannopyranose derivative. The glucopyranose derivatives have the advantage of being more readily synthesized since the preparation of the required beta-glucopyranoside is more facile than the corresponding beta-mannopyranoside.

Derivatization of the glycopyranose is typically by further reaction or reduction of the 2, 3, and/or 4 hydroxyl groups of the glycopyranose residue, or by substitution by methyl of the methylene hydrogens of the 6-CH$_2$OH group. Particularly preferred are (1) further glycosylation of the 3-OH to obtain a disaccharide or poly-saccharide, (2) methylation or reduction of the 4-OH, or glycosylation to obtain a disaccharide or poly-saccharide and (3) substitution of the R- or S-hydrogen of CH$_2$OH at position 6 by methyl, most preferably substitution by methyl for the H at the R-position.

The beta-pyranoside ring is stabilized by substitution for the H of the hemiacetal OH by a hydrophobic substituent, designated Y. Thus, the glycopyranosides represented by X have the general formula

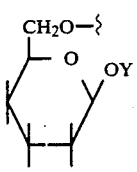

(4)

wherein Y is a hydrophobic hydrocarbyl moiety of 3-20 C, which may be unsubstituted or may be substituted by 1 or 2 substituents such as hydroxy, alkoxy (1-4C), carboxy, alkoxycarbonyl (1-5C), alkylcarbonyl (2-5C), amino, and the like. In addition, one or more of the methylene units in the hydrocarbyl residue may be replaced by a heteroatom, selected from the group consisting of N, S, and O. The precise nature of the substituent Y is not important except that it must be of sufficient hydrophobicity so as not to interfere with the properties of the compounds as acceptors or inhibitors. The hydrophobic nature of the substituent of Formula Y can also be taken advantage of to confer sufficient affinity to hydrophobic matrices to permit the compounds of the invention to be separated by reverse phase chromatography. Also, a substituent such as alkoxycarbonyl can be converted to a functional group useful in conjugating the compounds of the invention, if desired, to solid supports or to other moieties useful in targeting tissues.

Figure 3:
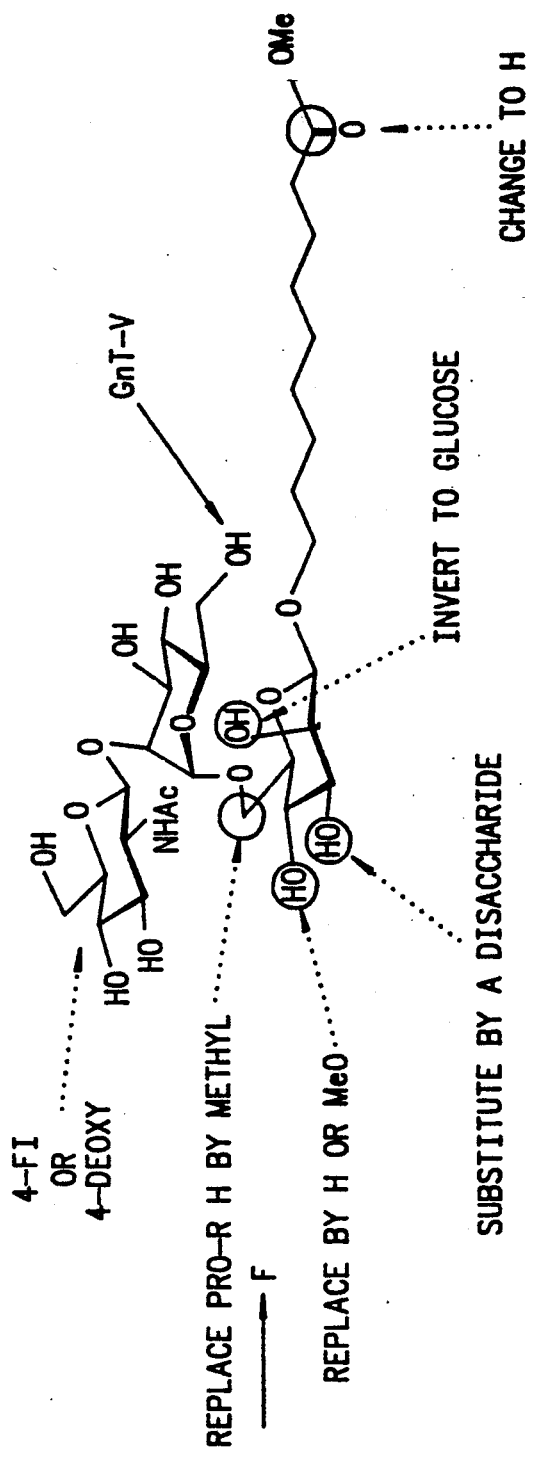
FIG. 3 illustrates various forms of derivatization of the acceptors and inhibitors of the invention.

FIG. 3 shows a diagram of some of the acceptor/inhibitor compounds, and preferred substitution and derivatization of the beta-glycopyranosyl residue represented by X.

Particularly preferred inhibitors are the following:
Y      6-O-[2-O-(2-acetamido-2-deoxy-beta-D-glucopyranosyl)-6-deoxy-alpha-D-mannopyranosyl]-beta-D-mannopyranoside;

Y  6-O-[2-O-(2-acetamido-2-deoxy-beta-D-glucopyranosyl)-6-deoxy-alpha-D-mannopyranosyl]-beta-D-glucopyranoside;

Y  6-O-[2-O-(2-acetamido-2-deoxy-beta-D-glucopyranosyl)-6-deoxy-alpha-D-mannopyranosyl]-4-deoxy-beta-D-xylo-hexopyranoside;

Y  6-O-[2-O-(2-acetamido-2-deoxy-beta-D-glucopyranosyl)-6-deoxy-alpha-D-mannopyranosyl]-4-O-methyl-beta-D-glucopyranoside;

Y  6-O-[2-O-(2-acetamido-2-deoxy-beta-D-glucopyranosyl)-6-deoxy-alpha-D-mannopyranosyl]-7-deoxy-alpha-L-glycero-D-gluco-heptopyranoside;

Y  6-O-[2-O-(2-acetamido-2-deoxy-beta-D-glucopyranosyl)-6-deoxy-alpha-D-mannopyranosyl]-7-deoxy-beta-D-glycero-D-gluco-heptopyranoside;

Y  6-O-[2-O-(2-acetamido-2-deoxy-4-fluoro-beta-D-glucopyranosyl)-6-deoxy-alpha-D-mannopyranosyl]-beta-D-mannopyranoside;

Y  6-O-[2-O-(2-acetamido-2-deoxy-4-fluoro-beta-D-glucopyranosyl)-6-deoxy-alpha-D-mannopyranosyl]-beta-D-glucopyranoside;

Y  6-O-[2-O-(2-acetamido-2-deoxy-4-fluoro-beta-D-glucopyranosyl)-6-deoxy-alpha-D-mannopyranosyl]-4-deoxy-beta-D-xylo-hexopyranoside;

Y  6-O-[2-O-(2-acetamido-2-deoxy-4-fluoro-beta-D-glucopyranosyl)-6-deoxy-alpha-D-mannopyranosyl]-4-O-methyl-beta-D-glucopyranoside;

Y  6-O-[2-O-(2-acetamido-2-deoxy-4-fluoro-beta-D-glucopyranosyl)-6-deoxy-alpha-D-mannopyranosyl]-7-deoxy-alpha-L-glycero-D-gluco-heptopyranoside;

Y  6-O-[2-O-(2-acetamido-2-deoxy-4-fluoro-beta-D-glucopyranosyl)-6-deoxy-alpha-D-mannopyranosyl]-7-deoxy-beta-D-glycero-D-gluco-heptopyranoside;

Y  6-O-[2-O-(2-acetamido-2,4-dideoxy-beta-D-glucopyranosyl)-6-deoxy-alpha-D-mannopyranosyl]-beta-D-mannopyranoside;

Y  6-O-[2-O-(2-acetamido-2,4-dideoxy-beta-D-glucopyranosyl)-6-deoxy-alpha-D-mannopyranosyl]-beta-D-glucopyranoside;

Y  6-O-[2-O-(2-acetamido-2,4-dideoxy-beta-D-glucopyranosyl)-6-deoxy-alpha-D-mannopyranosyl]-4-deoxy-beta-D-xylo-hexopyranoside;

Y  6-O-[2-O-(2-acetamido-2,4-dideoxy-beta-D-glucopyranosyl)-6-deoxy-alpha-D-mannopyranosyl]-4-O-methyl-beta-D-glucopyranoside;

Y  6-O-[2-O-(2-acetamido-2,4-dideoxy-beta-D-glucopyranosyl)-6-deoxy-alpha-D-mannopyranosyl]-7-deoxy-alpha-L-glycero-D-gluco-heptopyranoside; and Y  6-O-[2-O-(2-acetamido-2,4-dideoxy-beta-D-glucopyranosyl)-6-deoxy-alpha-D-mannopyranosyl]-7-deoxy-beta-D-glycero-D-gluco-heptopyranoside wherein Y is the hydrophobic substituent described above. Particularly preferred are the foregoing compounds wherein Y is selected from the group consisting of octyl and 8-methoxycarbonyloctyl.

Preferred acceptors are:

6-O-[2-O-(2-acetamido-2-deoxy-beta-D-glucopyranosyl)-alpha-D-mannopyranosyl]-beta-D-glucopyranoside;

Y  6-O-[2-O-(2-acetamido-2-deoxy-beta-D-glucopyranosyl)-alpha-D-mannopyranosyl]-4-deoxy-beta-D-xylo-hexopyranoside;

Y  6-O-2-O-(2-acetamido-2-deoxy-beta-D-glucopyranosyl)-alpha-D-mannopyranosyl]-4-O-methyl-beta-D-glucopyranoside;

Y  6-O-2[O-(2-acetamido-2-deoxy-beta-D-glucopyranosyl)-alpha-D-mannopyranosyl]-7-deoxy-alpha-L-glycero-D-gluco-heptopyranoside; and Y  6-O-[2-O-(2-acetamido-2-deoxy-beta-D-glucopyranosyl)-alpha-D-mannopyranosyl]-7-deoxy-beta-D-glycero-D-gluco-heptopyranoside;

wherein Y is as above defined. Especially preferred are the foregoing wherein Y is octyl.

PREPARATION OF THE ACCEPTORS AND INHIBITORS

The acceptors and inhibitors of the invention are prepared by effecting the (1-2) glycosylation by N-acetyl glucosamine of the acceptor 6-O-alpha-D-mannopyranosyl-beta-D-glycopyranoside. In the case of the inhibitor, the 6-deoxy form of the alpha-D-mannopyranosyl-beta-D-glycopyranoside residue will be substituted, and the donors include the 4-fluoro and 4-deoxy forms of N acetyl glucosamine.

An illustrative reaction scheme for the general approach is shown in FIG. 2. The structures of the numbered components are shown in FIG. 1. The first reaction (Rxn 1) of FIG. 2 shows the protection of the beta-glycopyranosyl residue "X", in this case illustrated by 8-methoxycarbonyloctyl mannose. Reactions 2-6 represent protection and preparation of the alpha-6-deoxy mannose; reactions 2 and 3 which effect the reduction of the hydroxyl at position 6 would be deleted in the preparation of the acceptors, and the compound of Formula 6 shown in FIG. 2 would be replaced by the penta-acetate. The remaining reactions in this group, 4-6, result in the suitably protected 1-halo alpha-mannoside or 1-halo 6-deoxy alpha-mannoside. Reactions 7 and 8 illustrate the production of the "minimally" disaccharide acceptor, alpha-Man(1-6)X or 6-deoxy-alpha-Man(1-6)X. Reaction 9 illustrates the formation of the (1-2) linkage of beta-GlcNAc to the minimally disaccharide acceptor, and reactions 10-11 the deprotection of the resulting "minimal" trisaccharide. The word "minimally" or "minimal" is used here because the glycopyranosyl residue of X may in turn be derivatized to obtain a di- or oligosaccharide, as explained above.

The preparation of six illustrative novel acceptors is described in detail by Srivastava, O. P., et al, *Carbohydrate Research* (1988) 179:137-161, which is incorporated herein by reference. Specifically, the syntheses of the acceptors:

Octyl  6-O-[2-O-(2-acetamido-2-deoxy-beta-D-glucopyranosyl)-alpha-D-mannopyranosyl]-beta-D-glucopyranoside;

Octyl  6-O-[2-O-(2-acetamido-2-deoxy-beta-D-glucopyranosyl)-alpha-D-mannopyranosyl]-4-deoxy-beta-D-xylo-hexopyranoside;

Octyl  6-O-[2-O-(2-acetamido-2-deoxy-beta-D-glucopyranosyl)-alpha-D-mannopyranosyl]-4-O-methyl-beta-D-glucopyranoside;

Octyl  6-O-[2-O-(2-acetamido-2-deoxy-beta-D-glucopyranosyl)-alpha-D-mannopyranosyl]-7-deoxy-alpha-L-glycero-D-gluco-heptopyranoside;

Octyl  6-O-[2-O-(2-acetamido-2-deoxy-beta-D-glucopyranosyl)-alpha-D-mannopyranosyl]-7-deoxy-beta-D-glycero-D-gluco-heptopyranoside; and Cyclohexylmethyl  6-O-[2-O-(2-acetamido-2-deoxy-beta-D-glucopyranosyl)-alpha-D-mannopyranoside]

using standard procedures are described.

It should be noted that in the last mentioned compound, the cyclohexylmethyl group putatively replaces the third saccharide residue—i.e., the beta-mannopyranosyl residue of the model trisaccharide portion. The ability of this compound to act as an acceptor is only about 25% of that exhibited by the remaining compounds. It is clear from this result, that while the compounds of the invention can include those wherein X, broadly construed, is a completely deoxygenated derivative of the saccharide residue at this position, these compounds as a group are less desirable than those which are at least trisaccharides. Accordingly, the preferred embodiments are those wherein the residue represented by X retains a beta-pyranose ring.

The synthesis of 8-methoxycarbonyloctyl 6-O-[2-O-(2-acetamido-2-deoxy-beta-D-glucopyranosyl)-alpha-D-mannopyranosyl]-beta-D-mannopyranoside is described in Tahir et al, *Can J Chem* (1986) 64:1771.

The synthesis of the inhibitors is illustrated herein. Briefly, as illustrated in FIG. 2, the 8-methoxycarbonyloctyl derivative of beta-D-glucopyranoside is converted to the benzyl derivative using standard methodology. Alternate forms of the beta-D-glucopyranoside having alternate embodiments of Y can be used as well.

In Reaction 2 of FIG. 2, methyl-alpha-D-mannopyranoside is reacted with triphenylphosphine and Niodosuccinimide to obtain the 6-iodo compound which is then reduced in Reaction 3 using hydrogen/Raney nickel and converted to the triacetylated form which is a mixture of the alpha and beta anomers. Reaction 4 converts the acyloxy group at the 1-position to a bromo and the series of Reactions 5-6 effects the conversion of the bromo at position 1 to the corresponding chloro derivative, which is suitable for reaction with the protected beta-D-glucopyranose acceptor, according to Reaction 7. Deprotection of the hydroxyl at position 2 of the 6-deoxy-mannosyl residue by treatment in sodium methoxide, as in Reaction 8, permits condensation with the 1-bromo protected glucosamine according to Reaction 9 and further deprotection by hydrolysis and reduction as shown in Reactions 10-12 results in the desired 8-methoxycarbonyl octyl 6-O-[2-O-(2-acetamido-2-deoxy-B-D-glucopyranosyl)alpha-D-6-deoxy-mannopyranosyl]-beta-D-glucopyranoside shown as Formula H in FIG. 2. For production of the compounds of the invention of Formulas 2B and 2C, the compound of Formula 14 in the 4-fluoro or 4-deoxy form is substituted for that shown.

Similar compounds of the invention with other embodiments for X are easily synthesized by substituting the desired glycopyranoside or derivative for the compound of Formula 1 in FIG. 2.

METHODS TO ASSAY GNT-V

The acceptors and inhibitors are useful to detect the presence and amount of GnT-V in a sample. For use as a diagnostic, the intracellular levels of GnT-V are measured. The cells are therefore lysed using sonication, osmotic pressure, or suitable mechanical means, and the cellular extracts or lysates are subjected to the assay.

One form of the assay is conducted by measuring the uptake of beta-GlcNAc from UDP-beta GlcNAc in the presence of the test extract by the acceptors of the invention. A variety of protocols to detect this uptake can be employed, including, for example, conjugation of the acceptor to a solid support and measuring the uptake of labeled beta-GlcNAc. An illustrative procedure is set forth, using as acceptor the trisaccharide 8-methoxycarbonyl octyl beta-GlcNAc(1-2)alpha-Man(1-6)beta-Man, in Pierce, M., et al, *Biochem Biophys Res Commun* (1987) 146:679-684, incorporated herein by reference. This procedure uses radiolabeled UDP-beta GlcNAc to provide a detection means for uptake of the substrate. Other protocols for measuring GnT-V using the acceptors of the invention can be adapted, for example, from the procedure used to measure the levels of GnT-V acceptor in EPO published application 134,292 to Abbott Laboratories.

To adapt the assay to assay for GnT-V using the inhibitors of the reaction, a crude extract of the sample cells can be used to provide a mixture of acceptors, rather than the use of synthetic analogs. In this assay, uptake of the general glycoside donor above, UDP-beta-GlcNAc, can again be used, but the mixture of GnT enzymes in the cell extract will simultaneously transfer the provided labeled donor to the acceptor mixture contained. Only GnT-V, however, is inhibited by the inhibitor compounds of the invention. Therefore, the level of inhibition shown in this assay will be a measure of the amount of GnT-V present.

FORMULATION AND ADMINISTRATION

The inhibitors of the invention are useful to inhibit metastasis of tumor cells in an afflicted subject by inhibition of the GnT-V enzyme, and thus inhibition of the synthesis of the branch-chain carbohydrates. The inhibitors can be formulated and administered as conventional pharmaceuticals using formulations such as those found, for example, in *Remington's Pharmaceutical Sciences*, Mack Publishing Company, Easton, PA, latest edition. Suitable compositions include solid compositions having conventional nontoxic solid carriers, for example, pharmaceutical grades of mannitol, lactose, starch, magnesium stearate, magnesium carbonate, and the like. Liquid compositions may also be used by dissolving or dispersing the inhibitors of the invention in aqueous media including buffer, Ringer's solution, Hank's solution, and the like. Suppository formulations employ, for example, polyalkylene glycols, such as propylene glycol, or other suitable supports. The composition may also contain minor amounts of nontoxic auxiliary substances such as wetting or emulsifying agents, pH buffering agents, and the like, for example, sodium acetate, sorbitan monolaurate, triethanolamine oleate, and so forth.

The inhibitors of the invention can be administered using parenteral or systemic administration using injection, such as subcutaneous, intramuscular, or intravenous injection, or administration via suppository or by oral administration. The formulation will be adapted to the mode of administration.

Suitable dosage levels are in the milligram-gram range per day for typical human subjects, or in the mg/kg range for animal subjects in general. The compounds are relatively nontoxic and have high excretion rates, so that relatively large amounts are required. Dosage levels suitable for a particular individual are optimized using general standard means known in the art used to devise dosage ranges for particular conditions. The optimal dosage level will depend, of course, upon the condition of the patient, the nature of the metastatic disease being treated, and the judgment of the attending physician. Administration over relatively long time periods of days and weeks will also be required as conditions typified by metastases are, in general, self-regenerating. Accordingly, repeated administration over indefinite time periods will be required in many instances, analogous, for example, to the administration of insulin to diabetics.

The following examples are intended to illustrate, but not to limit, the invention.

EXAMPLE 1

Preparation of Inhibitor:
8-methoxycarbonyloctyl-6-O-[2-O-(2-acetamido-2-deoxy-beta-D-glucopyranosyl)-6-deoxy-alpha-D-mannopyranosyl]-beta-D-glucopyranoside
(beta-GlcNAc(1-2)-6-deoxy-alpha-Man(1-6)-beta-Glu)

The synthesis of this compound is outlined in FIG. 2; the structures referred to in the description below are found in FIG. 1.

EXAMPLES

General Methods

TLC was performed on pre-coated plates of silica gel (60-$F_{254}$, Merck) with detection by quenching of fluorescence, or by charring, or both, after spraying with 5% $H_2SO_4$ in ethanol. Unless otherwise noted, column chromatography was performed on Silica Gel 60 Merck, 40-63 μm). Iatrobead refers to a beaded silica gel manufactured by Iatron Laboratories. Tokyo (product No. 6RS-8060). For gel filtration, Bio-Gel P-2 (200-400 mesh) (Bio-Rad Laboratories) was used. $^1$H-n.m.r. spectra were recorded at 360 MHz (Bruker WM-360) or 300 MHz (Bruker AM-300) with either tetramethylsilane ($\delta=0$ in $CDCl_3$) or acetone ($\delta=2.225$ in $D_2O$) as internal standard at ambient temperature. Only partial n.m.r. data re reported. Other spectral features were in accord with the proposed structures. The $^1$H-n.m.r. chemical shifts and coupling constants are reported as though they were first order. Unless otherwise noted, all reactions were carried out at ambient temperature, and, in the processing of reaction mixtures, solutions of organic solvents were washed with equal volumes of aqueous solutions. Organic solutions were dried over sodium sulfate prior to solvent removal on a rotary evaporator under the vacuum of a water aspirator with bath temperature of 40° C. or lower.

The following solvent systems have been designated by letters: A, ethyl acetate hexane 1:4 (v/v); B, ethyl acetate-hexane 2:5; C, ethyl acetate-hexane 1:2; D, ethyl acetate-hexane 1:1; E, ethyl acetate-toluene 1:5; F, dichloromethane-methanol 15:1; G, dichloromethane-methanol 9:1; H, dichloromethane-methanol 6:1; I, dichloromethane-methanol 10:1; J, dichloromethane-methanol-water 60:35:6.

Compound 1 was converted to 2 using standard procedures. The 6-deoxy-α-D-mannopyranosyl donor 7 was prepared as follows:

Reaction of methyl α-D-mannopyranoside 3 with triphenylphosphine and N-Iodosuccinimide, followed by acetylation of the crude product provided the 6-iodo-compound 4 (61%). Treatment of 4 with hydrogen gas in the presence of Raney nickel provided the 6-deoxy-sugar (99%) which was treated with sulfuric acid and in acetic anhydride to provide the anomeric acetate mixture 6 (91%). Reaction of 6 with HBr in acetic acid/dichloromethane gave 7. Compound 7 was converted to orthoester 8 (65%) following established procedures. Compound 8 was then de-O-acetylated (96%) and O-benzylated to provide 10 (68%). Treatment of 10 with trimethylsilylchloride then provided the glycosyl-donor 11.

Condensation of 2 and 11 (1.5 eq) in the presence of silver triflate and N,N,N',N'-tetramethylurea gave the α-linked disaccharide product 12 in 63% yield which was de-O-acetylated to provide 13. Condensation of 13 with the well known phthalimido bromide 14 then yielded the trisaccharide derivative 15 in 58% yield. The phthalimido group in 15 was removed using hydrazine and the product was treated with acetic anhydride in pyridine to provide 16 (89%). De-O-acetylation of 16 gave 17 (71%) from which the benzyl protecting groups were removed by catalytic hydrogenation over palladiumon-carbon to provide the inhibitor H (90%).

EXAMPLE I

Synthesis of Compound H

Triphenylphosphine (13.50 g, 51.5 mmol) was slowly added with stirring to a cooled solution of methyl α-D-mannopyranoside 3 (5.0 g, 25.8 mmol) and N-iodosuccinimide (11.6 g, 51.5 mmol) in N,N-dimethylformamide (200 mL). After heating the solution for 2.5 h at 50° C., methanol was added and the solution was concentrated to a syrup. Treatment of this syrup with acetic anhydride (10 mL) in pyridine (10 mL) for 8 h at room temperature followed by purification of the crude product by chromatography (solvent A) provided 4 ($R_f$ 0.49, solvent D) as a white solid (6.76 g, 61%) based on 3. $^1$H-n.m.r. ($CDCl_3$)δ: 5.321 (dd, 1H, $J_{2,3}=3.5$ Hz, $J_{3,4}=10.0$ Hz, H-3), 5.224 (dd, 1H, $J_{1,2}=2.0$ Hz, H-2), 5.118 (dd, 1H, $J_{4,5}=10.0$ Hz, H-4), 4.737 (d, 1H, H-1), 3.484 (s, 3H, —$OCH_3$).

A solution of 4 (2.23 g, 5.18 mmol) ($R_f$ 0.30, solvent E) and Raney nickel (1.20 g, 20.72 mmol) in methanol (40 mL) containing sodium acetate (0.85 g, 10.4 mmol) was agitated under hydrogen gas (1 atmospheric pressure) for 16 h. The catalyst was removed by filtration and the filtrate was concentrated in vaccuo. The residue was dissolved in dichloromethane (100 mL), washed with water, dried and evaporated to give 5 ($R_f$ 0.25, solvent E) as white solid (1.55 g, 98%). $^1$H-n.m.r. ($CDCl_3$)δ: 5.287 (dd, 1H, $J_{2,3}=3.5$ Hz, $J_{3,4}=10.0$ Hz, H-3), 5.237 (dd, 1H, $J_{1,2}=1.7$ Hz, H-2), 5.070 (dd, 1H, $J_{4,5}=10.0$ Hz, H-4), 4.631 (d, 1H, H-1), 3.859 (m, 1H, H-5), 3.390 (s, 3H, —$OCH_3$), 2.157, 2.051, and 1.990 (s, 3H, —$COCH_3$), 1.237 (d, 3H, J=6.1 Hz, H-6).

a solution of concentrated $H_2SO_4$ (44 μL) in acetic anhydride (0.83 mL) was added dropwise to a solution of 5 (1.02 g, 3.35 mmol) ($R_f$ 0.33, solvent C) in acetic anhydride (4.0 mL) at 0° C. The mixture was then stirred at room temperature for 30 min., poured into a stirring mixture of $CH_2Cl_2$ (100 mL) and ice cold saturated $NaHCO_3$ and the resulting mixture was stirred at room temperature for 30 min. The organic and aqueous layers were separated, and the aqueous layer was extracted with dichloromethane (2×25 mL). The dichloromethane solutions were combined and washed with saturated aqueous $NaHCO_3$ and $H_2O$, then concentrated. The residual syrup was purified by chromatography (solvent A) to yield 6 ($R_f$ 0.27, solvent C) as a syrup (2.22 g, 90%). The $^1$H-n.m.r. spectrum indicated the α/β ratio to be near 10:1. $^1$H-n.m.r. ($CDCl_3$)δ: 6.020 (d, $J_{1,2}=2.0$ Hz, H-1α), 5.841 (d, J=1.3 Hz, H-1β), 5.311 (dd, $J_{2,3}=3.5$ Hz, $J_{3,4}=10.0$ Hz, H-3α), 5.254 (dd, H-2α), 5.127 (dd, $H_{4,5}=10.0$ Hz, H-4α), 2.174, 2.164, 2.070, and 2.011 (s, 3H, $COCH_3$), 1.241 (d, 3H, J=6.0 Hz, H-6).

Compound 6 (1.0 g, 3.0 mmol) was dissolved in dry dichloromethane (25 mL) and 33% hydrogen bromide in acetic acid (4.0 mL) containing 3% acetic anhydride was added with stirring at 0° C. The resulting solution was warmed to room temperature and kept stirring for an additional 3 h by which time t.l.c. indicated the complete conversion of 6 ($R_f$ 0.27, solvent C) to the less polar product 7 ($R_f$ 0.38, solvent C). The mixture was diluted with dichloromethane (50 mL) and washed sequentially with ice water, saturated aqueous NaHCO$_3$ and ice water, then dried and evaporated. Toluene (3×2 mL) was added and re-evaporated to provide crude 7 as a syrup (H-1, δ6.260, $J_{1,2}$=2.0 Hz). This syrup was dissolved in chloroform (10 mL) and methanol (6.12 mL), followed by 2,6-lutidine (0.88 mL) were added. After 2 h at room temperature, the resulting mixture was diluted with dichloromethane (50 mL). washed twice with ice water, dried and concentrated to a syrup which was purified by chromatography (solvent A) to provide 8 ($R_f$ 0.29, solvent C) as a white powder (598 mg, 65% based on 6). $^1$H-n.m.r. (CDCl$_3$)δ: 5.424 (d, 1H, $J_{1,2}$=2.5 Hz, H-1), 5.067 (m, 2H, H-3 and H-4), 4.600 (dd, 1H, $J_{2,3}$=3.5 Hz, H-2), 3.274 (s, 3H, —OCH$_3$), 2.121 and 2.064 (s, 3H, —COCH$_3$), 1.734 (s, 3H, —CH$_3$), 1.237 (d, 3H, J=6.0 Hz, H-6).

Compound 8 (385 mg 1.27 mmol) was dissolved in dry methanol (2.0 mL) containing a trace of sodium methoxide. After 45 min., the solvent was evaporated providing 9 ($R_f$ 0.55, solvent H) as a syrup (268 mg, 96%) which was not further characterized. A solution of 9 (268 mg, 1.23 mmol) ($R_f$ 0.36, solvent D) in dry dimethylformamide (1.0 mL) was added slowly at 0° C. to a stirring suspension of NaH (88 mg, 3.65 mmol) in dimethylformamide (1.0 mL). Then benzyl bromide (0.43 mL, 3.65 mmol) was slowly added maintaining the temperature of reaction mixture in the range of 0°-5° C. The mixture was left for 17 h at room temperature, excess NaH was destroyed by the addition of methanol, the reaction mixture was diluted with dichloromethane and washed with water, dried and concentrated. The residual syrup was purified by chromatography (solvent A) providing 10 ($R_f$ 0.52, solvent D) as a white powder (331 mg, 68%). $^1$H-n.m.r. (CDCl$_3$)δ: 7.420-7.260 (m, 10H, aromatic), 5.287 (d, 1H, $J_{1,2}$=2.0 Hz, H-1), 4.384 (dd, 1H, $J_{2,3}$=4.0 Hz, H-2), 3.689 (dd, 1H, $J_{3,4}$=9.0 Hz, H-3), 3.489 (dd, 1H, $J_{4,5}$=9.0 Hz, H-4), 3.327 (m, 1H, H-5), 3.289 (s, 3H, OCH$_3$), 1.740 (s, 3H, —CH$_3$), 1.32 (d, 3H, J=6.0 Hz, H-6).

To a solution of 10 (213 mg, 0.53 mmol) ($R_f$ 0.38, solvent C) in dry dichloromethane (1.0 mL) was added chlorotrimethylsilane (0.122 mL, 0.96 mmol) dropwise under a nitrogen atmosphere. After 15 min., when the t.l.c. showed complete consumption of starting material, the solvent was evaporated and co-evaporated with toluene (3×2 mL) to provide 11 ($R_f$ 0.50, solvent C) which was not further characterized.

A mixture of alcohol 2 (0.194 g, 0.35 mmol) ($R_f$ 0.45, solvent C) and silvertrifluoromethanesulfonate (0.134 g, 0.52 mmol) was dried in vaccuo over phosphorouspentoxide. Dry dichloromethane (1.0 mL) was then added followed by N,N,N',N' tetramethylurea (80 μL, 0.69 mmol) and the mixture was stirred at 0° C. A solution of 11 (0.21 g, 0.69 mmol) ($R_f$ 0.52, solvent C) in dry dichloromethane (1.0 mL) was then added to the above mixture. After 1:5 h, the mixture was warmed to room temperature, diluted with dichloromethane (10 mL) and sym-collidine (60 μL), followed by silvertrifluoromethanesulfonate (0.130 g) were added to destroy excess 11. After 0.5 h, tetraethylammoniumbromide (100 mg) was added to precipitate excess silver which was removed by filtration and washed with dichloromethane (25 mL). The filtrate was washed twice with saturated sodium bicarbonate (50 mL) and twice with water (50 mL) before evaporation and purification by chromatography (solvent A). Disaccharide 12 ($R_f$ 0.57, solvent C) was obtained as white solid (0.267 g, 63%). $^1$H-n.m.r. (CDCl$_3$)δ: 7.360-7.200 (m, 25H, aromatic), 5.439 (dd, 1H, $J_{1',2'}$=2.0 Hz, $J_{2',3'}$=3.5 Hz, H-2'), 4.787 (d, H-1'), 4.360 (d, 1H, $J_{1,2}$=7.8 Hz, H-1), 2.147 (s, 3H, —COCH$_3$), 1.251 (d, J=6.0 Hz, H-6'), 0.867 (t, 3H, J=6.8 Hz, —CH$_3$).

Compound 12(267 mg, 0.287 mmol) ($R_f$ 0.57, solvent C) was dissolved in dry methanol (5 mL) containing a trace of sodium methoxide. After 5 h the solution was neutralized with Amberlite IR-120(H$^+$) resin, filtered and evaporated. Chromatography of the residue using 3:1 hexane-ethylacetate as eluent gave 13($R_f$ 0.34, solvent C) as a white solid (0.240 g, 94%). $^1$H-n.m.r. (CDCl$_3$) δ: 7.37-7.20 (m, 25H, aromatic), 4.854 (d, 1H, J=2.0 Hz, H-1), 4.360 (d, 1H, J=7.8 Hz, H-1), 3.804 (dd, 1H, $J_{2',3'}$=3.5 Hz, $J_{3',4'}$=9.5 Hz, H-3'), 2.427 (d, 1H, $J_{OH,2'}$=2.0 Hz, OH), 1.244 (d, 3H, J=6.0 Hz, H-6'), 0.867 (t, 3H, J=7 Hz, CH$_3$).

To a solution of 13(205 mg, 0.231 mmol) ($R_f$ 0.53, solvent D) in dry dichloromethane (4.0 mL), was added silvertrifluoromethanesulfonate (584 mg, 2.31 mmol), sym-collidine (0.31 mL, 2.31 mmol) and 4° A molecular sieve (1.0 g) and the resulting mixture was cooled to −50° C. A solution of bromide 14 (115 mg, 0.231 mmol) ($R_f$ 0.31, solvent D) in dry dichloromethane (4.0 mL) was then added and after 15 min. at −50° C. the reaction mixture was warmed to room temperature over a period of 1 h. T.l.c. showed the presence of approximately 25% of unreacted 13. The reaction mixture was then cooled to −50° C. and more 14 (115 mg, 0.231 mmol) in dry dichloromethane (4.0 mL) was added. After 15 min., the mixture was warmed to room temperature where it was kept for an additional 1 h. The reaction mixture was then diluted with dichloromethane (50 mL) and filtered through celite. The filtrate was washed sequentially with ice water, cold 1N hydrochloric acid, saturated sodium bicarbonate and finally water (50 mL each). Solvent was evaporated and the residue was purified by chromatography on Iatrobeads (solvent B) to provide trisaccharide 15 ($R_f$ 0.48, solvent D) as a syrup (120 mg, 58%). $^1$H-n.m.r. (CDCl$_3$) δ: 7.39-7.12 (m, 29H, aromatic), 5.887 (dd, 1H, $J_{2'',3''}$=9.5 Hz, $J_{3'',4''}$=10.5 Hz, H-3''), 5.451 (d, 1H, $J_{1'',2''}$=8.5 Hz, H-1''), 2.087, 2.054, and 1.900 (each s, 3H, COCH$_3$), 0.874 (t, 3H, J=7.0 Hz, CH$_3$), 0.524 (d, 3H, J=6.0 Hz, H-6').

A mixture of 15 (107 mg, 0.081 mmol) ($R_f$ 0.48, solvent D) and hydrazine hydrate (0.40 mL, 8.1 mmol) was refluxed in dry methanol (5.0 mL) for 5 h. The reaction mixture was then taken to dryness and the residue was dissolved in pyridine (2.0 mL) and acetic anhydride (2.0 mL) was added. After stirring for 16 h excess acetic anhydride was decomposed by dropwise addition of ethanol (10 mL) to the reaction mixture at 0° C. Solvent was evaporated and the residue was dissolved in dichloromethane (50 mL) and washed with 5% hydrochloric acid, saturated sodium bicarbonate and water (50 mL each). The solvent was evaporated and compound was purified by chromatography (solvent D) to give 16 ($R_f$ 0.28, solvent D) as a syrup (89 mg, 89%). $^1$H-n.m.r. (CDCl$_3$) δ: 7.38-7.14 (m, 25H, aromatic), 5.064 (dd, 1H, J=9.5, 10.5 Hz, H-4''), 4.760 (d, 1H, $J_{1',2'}$=2.0 Hz, H-1'), 4.384 (d, 1H, $J_{1,2}$=8.0 Hz, H-1), 2.037 (s, 6H, 2×COCH$_3$), 2.031 (s, 3H, COCH$_3$), 1.911 (s, 3H, NCOCH$_3$), 1.157 (d, 3H, J=6.0 Hz, H-6'), 0.870 (t, 3H, J=7.0 Hz, CH$_3$).

The trisaccharide 16 (45 mg, 0.037 mmol) (R$_f$ 0.67, solvent G) was de-O-acetylated as described for the preparation of 13. After removal of the resin by filtration, the solvent was evaporated to afford 17 (R$_f$ 0.31, solvent G) as a syrup (28 mg, 70%) which was not further characterized.

Compound 17 (28 mg, 0.026 mmol) (R$_f$ 0.73, solvent J) was dissolved in 98% ethanol (4.0 mL) and 5% palladium-on-charcoal (28 mg) was added. The mixture was stirred under one atmosphere of hydrogen gas for 17 h. The catalyst was removed by filtration and, after solvent evaporation, the residue was passed through a column of Bio-Gel P2 (2.5 cm×47 cm) using 10% aqueous ethanol as eluent. The carbohydrate containing fractions were pooled, concentrated, and lyophilized to provide H (R$_f$ 0.27, solvent J) as a white powder (14 mg, 85%). $^1$H-n.m.r. (D$_2$O) δ: 4.79 (H-1', obscured by HOD signal), 4.497 and 4.399 (each d, 1H, J=8.2 and 7.8 Hz, H-1 and H-1''), 4.072 (dd, 1H, J$_{1',2'}$=1.7, J$_{2',3'}$=3.5 Hz, H-2', decoupled by irradiation at δ4.79), 1.994 (s, 3H, NCOCH$_3$), 1.204 (d, J$_{5',6'}$=6.1 Hz, H-6'), 0.806 (t, 3H, J=7.0 Hz, octyl CH$_3$).

EXAMPLE 2

Effect of Inhibitors on GnT-V Activity

The procedure for assaying GnT-V activity is described in Tahir, S.H., et al, Can J Chem (1986) 64:1771, cited above, and incorporated herein by reference. This procedure is also described in Palcic, M. M., et al, *Glycoconjugate J* (1988) 5:49, and in Hindsgual, O., et al, *Carbohydrate Res* (1988) 173:263, both incorporated herein by reference. The latter two citations describe the results of this assay using various synthetic acceptors. The Palcic reference shows that the synthetic trisaccharide beta-GlcNAc(1-2)-alpha-Man(1-6)-beta-Man (conjugated to 8-methoxycarbonyloctyl through the hemiacetal hydroxyl) is an excellent acceptor for GnT-V, having an apparent K$_m$ of 80 μM. Confirmation of the structure of the product of the acceptor and donor beta-GlcNAc as having a 1-6 branch between the donor beta-GlcNAc and the acceptor alpha-mannose was demonstrated in the latter cited reference.

Conduct of the assay described in the Pierce reference above showed that conformationally restricted analog of the trisaccharide beta-GlcNAc(1-2)-6-deoxy-alpha-Man(1-6)-beta-Glu having a 6-C-methyl substituted for one of the 6-methylene hydrogens at the proR position of the glucopyranoside residue has a K$_m$ of 75 μM and a V$_{max}$ three times that of the unmethylated analog. The corresponding proS methylated compound was less effective as an acceptor.

The effects of the various inhibitors of the invention on the assay were tested according to the procedure of Srivastava, O. P., et al, *Carbohydrate Res* (1988) 179:137-161. This is basically the same procedure as that referred to above, except that incubations were performed for four hours at 37° C. The concentration of UDP-GlcNAc was 2 μM, containing a specific activity of 3.1×10$^6$ cpm/pmole in a total volume of 20 μl. Total protein concentration in the incubation mixture was 82 μg/20 μl, as determined by the Bradford assay using BSA as a standard.

The acceptor in this assay was octyl-beta-GlcNAc(1-2)-alpha-Man(1-6)-beta-Glu used at 80 μM.

For the compound octyl-beta-GlcNAc(1-2)-6-deoxy-alpha-Man(1-6)-beta-Glu, prepared in Example 1, the results were as follows:

TABLE 1

| uM Inhibitor | Sp. Activity (pmol GlcNAc/mg protein) |
|---|---|
| 0 | 80 |
| 80 | 21 |
| 200 | 8 |
| 500 | 3 |
| 2000 | 1 |

As shown in Table 1, an equimolar amount of inhibitor to acceptor shows a 75% inhibition of the enzyme. Calculations based on these data show K$_i$ of approximately 10 μM.

The inhibitor was specific for GnT-V. When the Triton X-100 extract of rabbit liver acetone powder was assayed for GnT-I using the acceptor, the 8-methoxycarbonyloctyl derivative of alpha-Man(1-3)-[alpha-Man(1-6)]-beta-Man, no inhibition was obtained, even at a concentration of 5,000 μM. Similar results were obtained in an assay for GnT-II using 8-methoxycarbonyloctyl beta-GlcNAc(1-2)-alpha-Man(1-3)[alpha-Man(1-6)]-beta-Man as acceptor.

EXAMPLE 3

Cell Permeability

A major obstacle to pharmaceutical utility for some compounds expected to act intracellularly is an inability to enter the cells whose metabolism is to be affected. In many cases, crossing the cell membrane is mediated by specific receptor mechanisms; in others, such as the case of the compounds of the invention, the nature of the compound is such that the cell membrane can be permeated nonspecifically. The following example demonstrates that compounds of the nature of those of the invention cross cell membranes. The model compound was an 8-methoxycarbonyloctyl trisaccharide which is a substrate for GnT-I.

Lec8 cells at a concentration of 2×10$^7$ cells/0.25 ml were preincubated in cyclohexamide for 2 hr. The 8-methoxycarbonyloctyl trisaccharide acceptor for the reaction of GnT-I was added at a concentration of 300 μM and the reaction mixtures were incubated at 37° C. with gentle shaking. At designated times, the cells in each tube were spun down, the supernatant removed, and the supernatant then applied to a Sep-Pak C18 column, which was washed with water and eluted with methanol.

The methanol eluate was dried and 500 μM UDP-Gal labeled with tritium at 1000 cpm/pmol was added to the residue along with 10 mM Mn$^{+2}$ and 5 milliunits of galactosyl transferase. After 6 hr of incubation at 37° C. a time adequate to complete any reaction catalyzed by the galactosyl transferase, the incubation mixture was reapplied to the C18 column, washed, and eluted with methanol. The methanol eluant was then processed for scintillation counting. The results are shown in Table 2:

TABLE 2

| Release of Modified Synthetic Acceptor for GnT-1 From Lec8 CHO Cells | | | |
|---|---|---|---|
| Incubation | GnT-1 Acceptor | Time (hr) | Galactose-transferred (pmol) |
| 1 | — | 0 | 0 |
| 2 | + | 0 | 0 |

TABLE 2-continued

Release of Modified Synthetic Acceptor for GnT-1 From Lec8 CHO Cells

| Incubation | GnT-1 Acceptor | Time (hr) | Galactose-transferred (pmol) |
|---|---|---|---|
| 3 | − | 3 | 0 |
| 4 | + | 3 | 0.38 |
| 5 | − | 6 | 0 |
| 6 | + | 6 | 1.09 |

The assay is based on the inability of the trisaccharide acceptor to accept a galactosyl residue from UDP-Gal unless it has first been extended intracellularly by the action of GnT-I. The results show that the trisaccharide acceptor has entered the cells to some extent after 3 hr and to a greater extent after 6 and has been converted to the tetrasaccharide acceptor for the galactosyl transferase by the intracellular enzyme GnT-I and intracellular GlcNAc donor.

I claim:

1. A compound useful as an acceptor for beta-GlcNAc from UDP-GlcNAc in a reaction catalyzed by N-acetyl glucosaminyl transferase-V (GnT-V) having the formula:

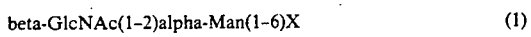

beta-GlcNAc(1-2)alpha-Man(1-6)X    (1)

wherein X is a glycopyranose or derivative thereof,
wherein said glycopyranose or derivative has the formula

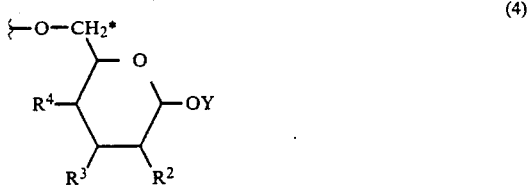

(4)

wherein Y is a noninterfering hydrophobic moiety;
R$^2$ is H,OH or H,H; R$^3$ is H,OH, H,H, or H,OZ, wherein Z is a mono- or oligosaccharide;
R$^4$ is H,OH; H,H; H,OCH$_3$, or H,OZ wherein Z is as above defined, and wherein one of the H* may be replaced by methyl;
with the proviso that X cannot be 8-methoxycarbonyl octyl beta-Man.

2. The compound of claim 1 wherein X is a beta-glucopyranose or a derivative thereof.

3. The compound of claim 1 which is selected from the group consisting of
Y   6-O-[2-O-(2-acetamido-2-deoxy-beta-D-glucopyreanosyl)-alpha-D-mannopyranosyl]-beta-D-glucopyranoside;
Y   6-O-[2-O-(2-acetamido-2-deoxy-beta-D-glucopyranosyl)-alpha-D-mannopyranosyl]-4-deoxy-beta-D-xylo-hexopyranoside;
Y   6-O-[2-O-(2-acetamido-2-deoxy-beta-D-glucopyranosyl)-alpha-D-mannopyranosyl]-4-O-methyl-beta-D-glucopyranoside;
Y   6-O-[2-O-(2-acetamido-2-deoxy-beta-D-glucopyranosyl)-alpha-D-mannopyranosyl]-7-deoxy-alpha-L-glycero-D-gluco-heptopyranoside;
Y   6-O-[2-O-(2-acetamido-2-deoxy-beta-D-glucopyranosyl)-alpha-D-mannopyranosyl]-7-deoxy-beta-D-glycero-D-gluco-heptopyranoside; and
cyclohexylmethyl   6-O-[2-O-(2-acetamido-2-deoxy-beta-D-glucopyranosyl)-alpha-D-mannopyranoside];
wherein Y is a substituent at the 1-position of the glycopyranose represented by X and is a hydrophobic hydrocarbyl moiety of 3-20C, which may be unsubstituted or may be substituted by 1 or 2 substituents selected from the group consisting of hydroxy, alkoxy (1-4C), carboxy, alkoxycarbonyl (1-5C), alkylcarbonyl (2-5C), and amino, and wherein one or more of the methylene units in the hydrocarbyl residue may be replaced by a heteroatom selected from the group consisting of N, S and O, and wherein Y can further be coupled to a solid support.

4. The compound of claim 3 wherein Y is octyl.

5. The compound of claim 1 wherein X is a glucopyranose.

6. The compound of claim 1 wherein at least one of R$^3$ and R$^4$ is H,OZ wherein Z is a monosaccharide.

7. The compound of claim 1 wherein one of the H* is replaced by methyl.

8. A method to assay the level of GnT-V in a sample, which method comprises:
adding to the sample a measured amount of the compound of claim 1, and
measureing the amount of beta-BlcNAc transferred from UDP-ClcNAc to said compound of claim 1.

9. An inhibitor of GnT-V having the formula:

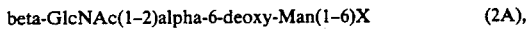

beta-GlcNAc(1-2)alpha-6-deoxy-Man(1-6)X    (2A), or

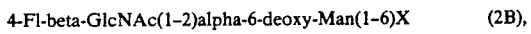

4-Fl-beta-GlcNAc(1-2)alpha-6-deoxy-Man(1-6)X    (2B), or

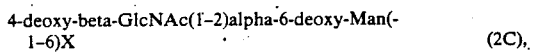

4-deoxy-beta-GlcNAc(1-2)alpha-6-deoxy-Man(-1-6)X    (2C), wherein X is a beta-glycopyranose or derivative thereof
wherein said glycopyranose or derivative has the formula

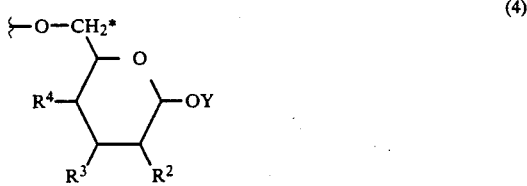

(4)

wherein Y is a noninterfering hydrophobic moiety;
R$^2$ is H, OH or H,H; R$^3$ is H,OH, H,H, or H,OZ, wherein Z is a mono- or oligosaccharide;
R$^4$ is H,OH; H,H; H,OCH$_3$, or H,OZ wherein Z is as above defined, and wherein one of the H* may be replaced by methyl.

10. The compound of claim 9 wherein X is selected from a beta-glucopyranose or beta-mannopyranose, and derivatives thereof.

11. The compound of claim 10 wherein X is selected from the group consisting of
Y beta-D-glucopyranoside;
Y beta-D-mannopyranoside;
Y 4-deoxy-beta-D-xylo-hexopyranoside;
Y 4-O-methyl-beta-D-glucopyranoside;

Y 7-deoxy-alpha-L-glycero-D-gluco-heptopyranoside; and

Y 7-deoxy-beta-D-glycero-D-gluco-heptopyranoside;

wherein Y is a substituent at the 1-position of the glycopyranose represented by X and is a hydrophobic hydrocarbyl moiety of 3-20C, which may be unsubstituted or may be substituted by 1 or 2 substituents selected from the group consisting of hydroxy, alkoxy (1-4C), carboxy, alkoxycarbonyl (1-5C), alkylcarbonyl (2-5C), and amino, and wherein one or more of the methylene units in the hydrocarbyl residue may be replaced by a heteroatom selected from the group consisting of N, S and O, and wherein Y can further be coupled to a solid support.

12. The compound of claim 11 wherein Y is a hydrocarbyl of 3-20C which is unsubstituted or is substituted with 1-2 substituents selected from the group consisting of alkoxy (1-4C) and alkoxycarbonyl (2-5C).

13. The compound of claim 12 wherein Y is selected from octyl and 8-methoxycarbonyl octyl.

14. The compound of claim 10 wherein X is a glucopyranose.

15. The compound of claim 10 wherein at least one of $R^3$ and $R^4$ is H,OZ wherein Z is a monosaccharide.

16. The compound of claim 10 wherein one of the H* is replaced by methyl.

17. A pharmaceutical composition for inhibition of metastasis, which composition comprises as active ingredient one or more compounds of claim 9 in admixture with a suitable pharmaceutical carrier.

18. A method to measure the level of GnT-V in a sample containing a multiplicity of GnT enzymes and GnT acceptors, which method comprises:

adding to a portion of said sample an effective amount of the inhibitor of claim 6, followed by incubating said sample to which the inhibitor of claim 6 has been added in the presence of the carbohydrate donor UDP-GlcNAc, and incubating another portion of said sample to which said inhibitor of claim 6 has not been added in the presence of the carbohydrate donor UDP-GlcNAc, and comparing the amount of GlcNAc transferred to acceptor in the presence and absence of the compound of claim 9, wherein the diminution of the amount of GlcNAc transferred to acceptor in the presence of said inhibitor as compared to that transferred in the absence of said inhibitor is a measure of the level of GnT-V in said sample.

* * * * *